US00PP21865P2

(12) United States Plant Patent
Cain et al.

(10) Patent No.: US PP21,865 P2
(45) Date of Patent: Apr. 12, 2011

(54) PLUM TREE NAMED 'SUPLUMTHIRTYNINE'

(50) Latin Name: *Prunus salicina*
Varietal Denomination: Suplumthirtynine

(75) Inventors: David W. Cain, Bakersfield, CA (US); Terry Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 12/583,127

(22) Filed: Oct. 29, 2009

(51) Int. Cl.
*A01H 5/00* (2006.01)

(52) U.S. Cl. ..... Plt./184
(58) Field of Classification Search ..... Plt./184
See application file for complete search history.

(56) References Cited

U.S. PATENT DOCUMENTS

PP2,747 P 6/1967 Garabedian

*Primary Examiner* — Susan B McCormick Ewoldt
(74) *Attorney, Agent, or Firm* — Knobbe, Martens, Olson & Bear, LLP

(57) ABSTRACT

A new and distinct plum tree variety, *Prunus salicina*, cv. 'Suplumthirtynine' is characterized by ripening very late in the harvest season, about three weeks later than 'Suplumsix' (U.S. Plant Pat. No. 2,747). The new variety is further characterized by relatively large-sized fruit for the season and amber-colored flesh.

1 Drawing Sheet

Latin name of the genus and species claimed: *Prunus salicina.*

Variety denomination: 'Suplumthirtynine'.

BACKGROUND AND SUMMARY OF THE INVENTION

This invention relates to the discovery and asexual propagation of a new and distinct variety of plum, *Prunus salicina* cv. 'Suplumthirtynine'. The new variety was first hybridized by David Cain in 1998 and selected by Terry Bacon in 2002 as breeder number: 'PL186YB'. The new variety was first evaluated by Terry Bacon near Wasco, Calif. in Kern County. The variety 'Suplumthirtynine' was originated by hybridization.

The new variety 'Suplumthirtynine' is characterized by ripening very late in the season. In the Wasco, Calif. area, the harvest season, September 10 through October 5, is about three weeks later than that of 'Suplumsix' (the subject of U.S. Plant Pat. No. 2,747), the variety it most closely resembles in appearance. The new variety 'Suplumthirtynine' is further characterized by relatively large-sized fruit for the season (average fruit diameter approximately 64 mm, compared to approximately 60 mm for 'Suplumsix') and amber-colored flesh.

The seed parent is an unpatented breeding selection, '91P-024', and the pollen parent is an unpatented breeding selection, '92-P023'. The parent varieties were first crossed in March of 1998, with the date of planting of the progeny being January 1999, and the date of first flowering being March 2001. The new plum variety 'Suplumthirtynine' was first asexually propagated by Terry Bacon near Wasco, Kern County, Calif. in January 2003, by grafting.

The new variety 'Suplumthirtynine' is distinguished from its seed parent, '91P-024', in that the new variety ripens about twelve weeks later than '91P-024'. The new variety 'Suplumthirtynine' also has amber-colored flesh compared to the reddish flesh of the seed parent.

The new variety 'Suplumthirtynine' is distinguished from its pollen parent, '92P-023', in that the new variety ripens about ten weeks later than '92P-023'. The new variety 'Suplumthirtynine' also has amber-colored flesh compared to the reddish flesh of the pollen parent.

The new variety 'Suplumthirtynine' has been shown to maintain its distinguishing characteristics through successive asexual propagations by, for example, budding and grafting.

BRIEF DESCRIPTION OF THE PHOTOGRAPH

The accompanying color photographic illustration shows typical specimens of the foliage and fruit of the present new plum variety 'Suplumthirtynine'. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England.

The descriptive matter which follows pertains to 7 year old 'Suplumthirtynine' plants, grown in the vicinity of Wasco, Kern County, Calif., during September 2008, and is believed to apply to plants of the variety grown under similar conditions of soil and climate elsewhere.

TREE

General: (Measurements taken on 7 year old tree unless otherwise noted.)

*Size.*—Medium. Normal for most plum varieties. Reaches a height of approximately 3 meters with normal pruning.

*Spread.*—Normal for most plum varieties. Approximately 3 meters.

*Vigor.*—Moderately vigorous.

*Growth.*—Semi-upright.

*Productivity.*—Very productive. Fruit set is usually two or more times desired amount for marketable size fruit.

*Form.*—Vase formed.

*Bearer.*—Regular.

*Fertility.*—Unknown.

*Canopy density.*—Medium-dense.

*Hardiness.*—Half-hardy in all fruit growing areas of California.

*Disease resistance/susceptibility.*—No specific testing for relative plant disease resistance/susceptibility has been undertaken. Under close observation in Kern County, Calif., no particular plant/fruit disease resistance/susceptibility has been observed.

Trunk: (Measurements at approximately 30 cm above soil line.)

*Diameter.*—Approximately 22 cm, varies with soil type, fertility, climatic conditions and cultural practices.

*Texture.*—Medium shaggy, increases with age of tree.

*Trunk color.*—About Grey-green 198A to Grey-orange 166D; becomes darker with age.

Branches: (Measurements at approximately 90 cm above soil line.)

*Size.*—Diameter ranges from approximately 7 to approximately 9 cm.

*Texture.*—Smooth on first year wood, increasing roughness with tree age.

*Color.*—Branches vary from about Grey-brown 199B to Brown 200B.

*Number of lenticels.*—Medium, about 2-3/cm$^2$.

*Lenticels density.*—Approximately 1-4 per cm$^2$.

*Lenticels color.*—About 198A.

*Lenticels size.*—Medium, about 2 mm.

*Lenticels length.*—Approximately 4 mm.

*Lenticels width.*—Approximately 2 mm.

Flowering shoots: (Data taken in July at midpoint of 2-year old flowering shoots.)

*Size.*—Average diameter approximately 5 mm.

*Color.*—Topside: About Grey-green 198B to Brown 200D. Underside: About Grey-orange 165B to Brown 200D.

*Internode length.*—Medium; approximately 25 mm. Midway on flowering shoot.

*Flowering shoot lenticels.*—Plentiful, minute. Color: About Grey-orange 177A. Diameter: Approximately 0.2 mm.

*Flowering shoot leaf buds.*—Shape: Obovate. Width: Approximately 2 mm. Length: Approximately 2.5 mm. Color: About Grey-orange 165A.

*Flowering shoot flower buds.*—Shape: Obovate, borne on short spurs, approximately 14-40 mm long. Width: Approximately 2 mm. Length: Approximately 2.5 mm. Color: About Grey-orange 165A. Number per node: Usually 2. Position: Free.

*Flower bud distribution.*—Generally 2 or more, on spurs.

*Ratio of wood (leaf) buds to flowering buds.*—½.

FOLIAGE

Leaves:

*Size.*—Medium.

*Average length.*—Medium; approximately 94-117 mm.

*Average width.*—Medium; approximately 42-45 mm.

*Thickness.*—Medium, about 0.3 mm.

*Color.*—Upper surface: About 137B. Lower surface: About 138B.

*Form.*—Elliptic.

*Tip.*—Acuminate.

*Base.*—V-shaped.

*Margin.*—Crenate.

*Venation.*—Pinately net veined.

*Vein color.*—About 147C on lower surface.

*Surface texture.*—Smooth.

*Leaf blade (ratio of length to width).*—Medium.

*Shape in the cross section.*—Convex.

*Profile.*—Flat.

*Leaf blade tip.*—Curved downward.

*Undulation of margin.*—Slight.

Petiole:

*Average length.*—Medium; approximately 16 mm.

*Average diameter.*—Approximately 2 mm.

*Color.*—About 147D.

Leaf stipules:

*Number per leaf bud.*—Rare on flowering shoots in July.

*Typical length.*—Approximately 5 mm.

*Color.*—About 199B.

*Persistence.*—Falls off.

Leaf glands:

*Form.*—Globose.

*Average number.*—Most leaves have none. Where they exist about two/leaf.

*Position.*—On leaf base.

*Average size.*—Small; approximately 0.5 mm.

*Color.*—About 199B.

FLOWERS

General:

*Flower blooming period.*—First bloom: Approximately March 1. Full bloom: Approximately March 6.

*Duration of bloom.*—Medium; approximately 12 days.

*Diameter of fully opened flower.*—Medium, approximately 24 mm.

*Flower aroma.*—Slight aroma.

*Shape.*—Rosaceous.

Peduncle:

*Length.*—Medium; approximately 10 mm.

*Diameter.*—Medium; approximately 1 mm.

*Color.*—About Yellow-green 144B.

*Pubescence.*—Absent.

Petals:

*Number.*—5.

*Arrangement.*—Overlapping slightly.

*Length.*—Approximately 10 mm.

*Diameter.*—Approximately 10 mm.

*Shape.*—Circular.

*Apex shape.*—Rounded.

*Base shape.*—Narrows at point of attachment.

*Color.*—About White 155D.

*Surface texture.*—Smooth.
*Margins.*—Slightly undulating.
*Claw length.*—Medium, approximately 1.5 mm.
*Margin waviness.*—Medium, smooth and slightly wavy.
*Base angle.*—Narrow.
*Division of upper margin.*—Entire.
*Pubescence of inner surface.*—Absent.
*Pubescence of outer surface.*—Absent.

Sepals:
*Number.*—5.
*Length.*—Approximately 3 mm.
*Diameter.*—Approximately 2 mm.
*Shape.*—Elliptic.
*Color.*—About Yellow-green 144A.
*Surface texture.*—Smooth.
*Margins.*—Entire.
*Positioning.*—Adpressed or touching petals.
*Pubsencence of inner surface.*—Absent.
*Pubescence of outer surface.*—Absent.

Stamens:
*Number.*—Ranges from approximately 20 to approximately 30.
*Average length.*—Approximately 7 mm.
*Filament color.*—About white 155D.
*Anther color.*—About Grey-orange 167A.
*Flower pollen color.*—About Grey-orange 167A.
*Position.*—Perigynous.

Pistil:
*Number.*—Usually one, occasionally two.
*Average length.*—Approximately 9 mm.
*Ovary diameter.*—Approximately 0.8 mm.
*Pubescence.*—None.
*Stigma extension in comparison to anthers.*—Usually below.
*Frequency of supplementary pistils.*—Few.
*Style pubescence* (*of base*).—Absent.

Receptacle:
*Depth.*—Medium.
*Pubescence of inner surface.*—Absent.
*Pubescence of outer surface.*—Absent.

FRUIT

General: (Description taken near Wasco, Kern County, Calif.)
*Harvest.*—Date of first pick: Approximately September 10. Date of last pick: Approximately October 5.

Maturity when described: Firm.
Season ripening: Very late.
Position of maximum diameter: Towards the middle.
Symmetry about the suture: Nearly symmetric.

Size:
*Length* (*stem end to apex*).—Approximately 60 mm.
*Diameter perpendicular to suture plane.*—Approximately 64 mm.
*Average weight.*—Approximately 160 gm.

Form:
*Viewed from apex.*—Rounded, nearly symmetrical.
*Viewed from side, facing suture.*—Rounded, nearly symmetrical.
*Viewed from side, perpendicular to suture.*—Rounded, nearly symmetrical.

Apex shape: Rounded.

Fruit stem cavity:
*Shape.*—Flaring, rounded.
*Depth.*—Approximately 0.5 cm.
*Breadth.*—Approximately 1 cm.
*Width.*—Medium, approximately 10 mm.

Fruit stem:
*Length.*—Approximately 10 mm.
*Diameter.*—Approximately 2 mm.
*Color.*—About 146C.

Fruit skin:
*Thickness.*—Medium, approximately 0.3 mm.
*Adherence to flesh.*—Medium.
*Surface texture.*—Smooth.
*Pubescence.*—None.
*Bloom.*—Medium, slight bloom.
*Ground color.*—About 161C.
*Overcolor.*—About 183A.
*Taste.*—Mild.
*Reticulation.*—Absent.
*Roughness.*—Absent.
*Tendency to crack.*—Slight in wet season.

Flesh:
*Ripens.*—Evenly.
*Texture.*—Firm, juicy.
*Fibers.*—Few.
*Flavor.*—Sweet-mild.
*Brix.*—Approximately 20°.
*Juice.*—Abundant to moderate.
*Aroma.*—Noticeable when ripe.
*Color.*—About 161C.
*Anthocyanin color under skin.*—Absent.
*Anthocyanin color of flesh.*—Absent.
*Anthocyanin color around stone.*—Absent.
*Acidity.*—Medium-low.
*Sugar content.*—High.
*Eating quality.*—Good.
*Stone/flesh ratio.*—1/28.
*Firmness.*—Medium-firm.

Pit cavity size:
*Length* (*diameter in line with suture plane*).—Approximately 16 mm.
*Diameter perpendicular to suture plane.*—Approximately 10 mm.
*Color.*—About 161A.

Fruit use: Fresh market.

Fruit shipping and keeping quality: Good, holds well in cold storage and maintains good firmness and eating quality, minimal bruising and scarring in packing and shipping trials.

Suture line: Inconspicuous.

Stone: (Measurements taken on dried stones.)
*Stone freeness.*—Semi-free to Free.
*Degree of adherence to flesh.*—Weak.
*Stone size.*—Size compared to fruit: Small. Length (diameter in line with suture plane): Approximately 16 mm. Diameter perpendicular to suture plane: Approximately 10 mm. Width of stalk end: Medium; approximately 2-4 mm. Angle of stalk end: Obtuse. Hilum: Somewhat broad.
*Stone form.*—Viewed from side: Nearly oval, somewhat asymmetric. Viewed from ventral side: Nearly oval. Viewed from stem end: Nearly Oval.
*Stone shape.*—Base shape: Nearly straight. Apex shape: Obtuse with somewhat pointed tip.
*Stone surface.*—Somewhat irregularly furrowed and pitted throughout.
*Stone halves.*—Nearly equal.
*Stone ridges.*—Rounded and Continuous.

*Stone outgrowing keel.*—Partially developed.
*Stone tendency to split.*—Slight in wet season.
*Stone color.*—About 165C.
*Position of maximum.*—Toward middle.
*Pits.*—Irregular.

What is claimed is:

1. A new and distinct plum tree as herein described and illustrated.

* * * * *

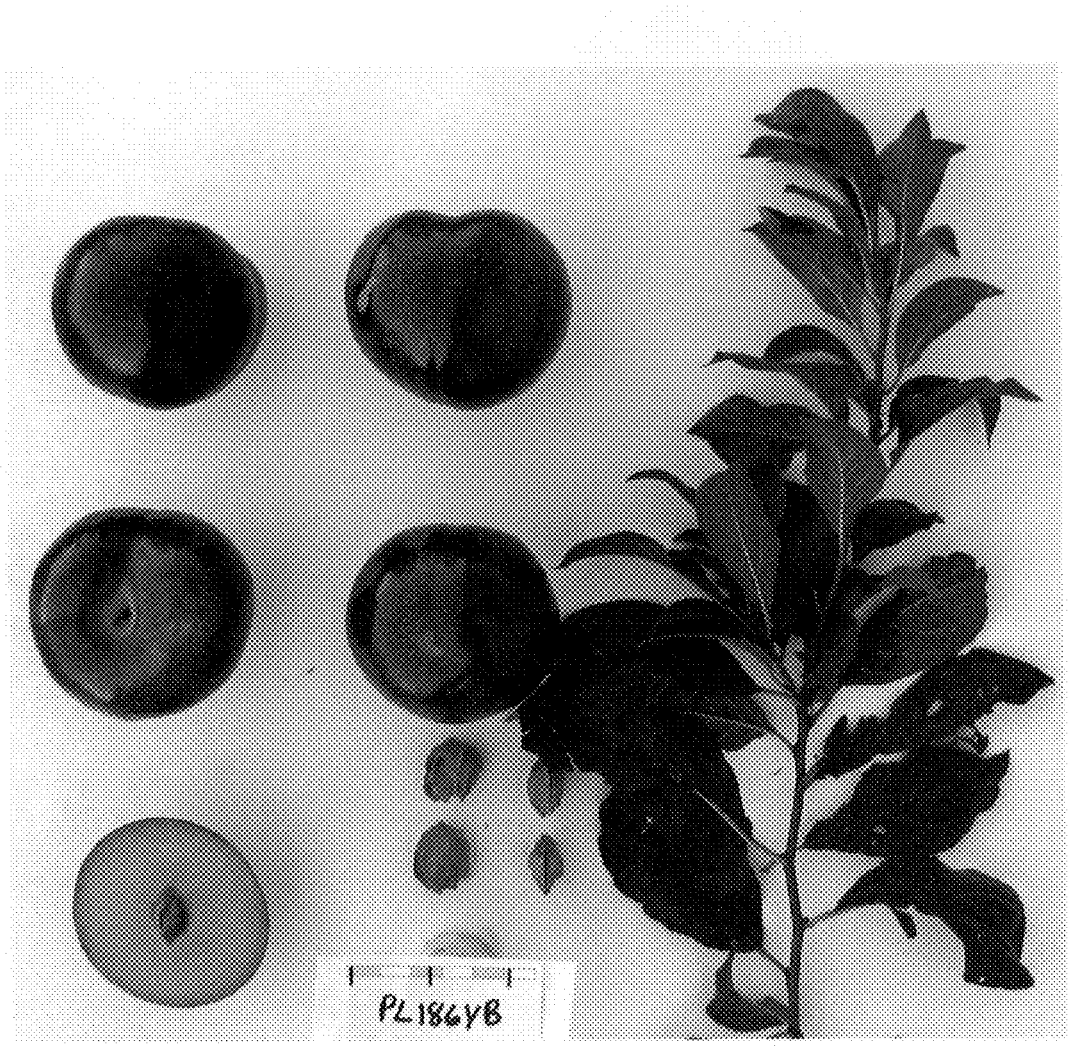
PL186YB